United States Patent [19]

Bowler

[11] 4,241,215
[45] Dec. 23, 1980

[54] PROSTANE DERIVATIVES

[75] Inventor: Jean Bowler, Macclesfield, England

[73] Assignee: Imperial Chemical Industries Limited, London, England

[21] Appl. No.: 713,505

[22] Filed: Aug. 11, 1976

[30] Foreign Application Priority Data

Aug. 22, 1975 [GB] United Kingdom ............... 34969/75

[51] Int. Cl.³ .......................................... C07C 177/00
[52] U.S. Cl. ....................................... 560/55; 560/61;
560/62; 562/465; 562/471; 562/472; 260/410;
260/410.5; 260/404; 260/408; 260/410.9 R;
424/308; 424/309
[58] Field of Search ..................... 260/473, 410, 410.5,
260/404, 408, 410.9; 560/55, 61, 62; 562/465,
471, 472; 424/308, 309

[56] References Cited

FOREIGN PATENT DOCUMENTS 2456051  7/1974  Fed. Rep. of Germany ........... 260/473
738554  10/1973  South Africa ........................... 260/473

OTHER PUBLICATIONS

Derwent Abst., 38259V/21
Derwent Abst., 55893W/34

Primary Examiner—Paul J Killos
Attorney, Agent, or Firm—Cushman, Darby & Cushman

[57] ABSTRACT

The disclosure relates to novel 4-cis-prostenoic acid derivatives, for example 16-(3-chlorophenoxy)-9α,11α,15-trihydroxy-17,18,19,20-tetranor-4-cis, 13-trans-prostadienoic acid, to chemical processes for their manufacture, to pharmaceutical and veterinary compositions containing them, and to the use of the compounds in a method of luteolysis, a method of inhibiting blood platelet aggregation, and a method of inhibiting gastric acid production.

9 Claims, No Drawings

PROSTANE DERIVATIVES

This invention relates to novel prostane derivatives, and in particular it relates to novel 4-prostene derivatives possessing high luteolytic activity. The new compounds are therefore useful as contraceptives or for control of the oestrous cycle in animals. Some of the compounds also possess high activity in preventing blood platelet aggregation. The compounds may also be useful for the induction of labour or the early termination of pregnancy, or as hypotensives, for the relief of bronchospasm or the inhibition of gastric acid production.

According to the invention there is provided a prostane derivative of the formula:

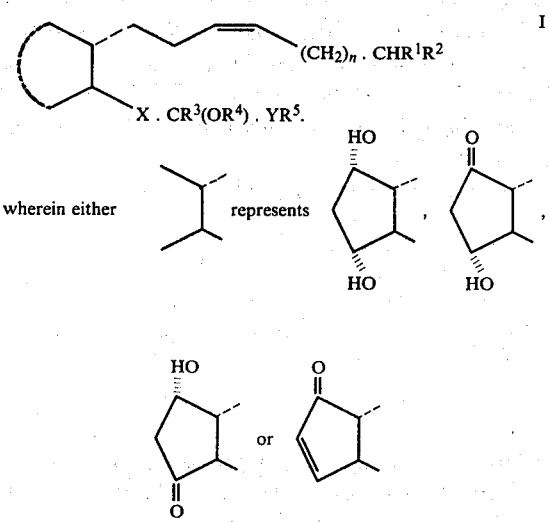

, and $R^1$ is a carboxy radical, or a $C_{2-12}$ alkoxycarbonyl radical, or,

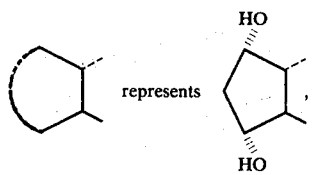

and $R^1$ is a hydroxymethyl or $C_{2-12}$ alkoxymethyl radical, $R^2$, $R^3$ and $R^4$, which may be the same or different, are each a hydrogen atom or a $C_{1-5}$ alkyl radical, X is an ethylene or trans-vinylene radical, Y is a $C_{1-5}$ alkyleneoxy radical, wherein the oxygen atom is bonded to $R^5$, a $C_{1-5}$ alkylene radical, or a direct bond, $R^5$ is a phenyl or naphthyl radical which is unsubstituted or is substituted by one or more substituents selected from halogen atoms, nitro radical and $C_{1-5}$ alkyl, alkoxy and halogenoalkyl radicals, and n is 1 to 4, and for those compounds wherein $R^1$ is a carboxy radical, the pharmaceutically or veterinarily acceptable salts thereof.

A suitable value for $R^1$ when it is a $C_{2-12}$ alkoxycarbonyl radical is, for example, a methoxycarbonyl, ethoxycarbonyl, butoxycarbonyl or decyloxycarbonyl radical, especially such a radical of 2 to 5 carbon atoms, and particularly a methoxycarbonyl radical; and a suitable value for $R^1$ when it is a $C_{2-12}$ alkoxymethyl radical is, for example, a methoxymethyl, ethoxymethyl, butoxymethyl or decyloxymethyl radical, especially such a radical of 2 to 5 carbon atoms.

A suitable value for any of $R^2$, $R^3$ and $R^4$ when it is a $C_{1-5}$ alkyl radical is, for example, a methyl, ethyl, propyl, butyl or pentyl radical, especially a methyl or ethyl radical and particularly a methyl radical.

n is preferably 1 or 2.

A suitable value for Y when it is a $C_{1-5}$ alkyleneoxy radical is, for example, a methyleneoxy, ethyleneoxy, trimethyleneoxy, ethylideneoxy, isopropylideneoxy, [—C(CH$_3$)$_2$O—], propylideneoxy, 1-methylpropylideneoxy [—C(CH$_3$)(C$_2$H$_5$).O—] or 1-ethylpropylideneoxy [—C(C$_2$H$_5$)$_2$.O—] radical, particularly a methyleneoxy or isopropylideneoxy radical, and a suitable value for Y when it is a $C_{1-5}$ alkylene radical is, for example, a methylene, ethylene, methylethylene, trimethylene, ethylidene, propylidene, isopropylidene, 1-methylpropylidene or 1-ethylpropylidene radical, and particularly a methylethylene radical (—CHMe.CH$_2$—) in which the —CH$_2$— part is bonded to $R^5$.

A suitable halogen substituent in $R^5$ is, for example, a chlorine, fluorine, bromine or iodine atom, especially a chlorine atom; a suitable $C_{1-5}$ alkyl or alkoxy substituent in $R^5$ is, for example, a methyl, ethyl, methoxy or ethoxy radical; and a suitable $C_{1-5}$ halogenoalkyl substituent is, for example, a chloroalkyl or fluoroalkyl radical, such as a trifluoromethyl radical. Preferred values for $R^5$ contain not more than two substituents, and particular values are phenyl, chlorophenyl, especially 3-chlorophenyl, and trifluoromethylphenyl, especially 4-trifluoromethylphenyl, radicals.

A suitable pharmaceutically or veterinarily acceptable salt is, for example, an ammonium, alkylammonium containing 1 to 4 $C_{1-5}$ alkyl radicals, alkanolammonium containing 1 to 3 2-hydroxyethyl radicals, or alkali metal salt, for example an ammonium, triethylammonium, ethanolammonium, diethanolammonium, sodium or potassium salt.

It will be observed that the novel prostane derivatives of the formula I contain at least three asymmetrically substituted carbon atoms, namely the two carbon atoms at which the side-chain are attached to the ring (the relative stereochemistry at these two positions is fixed in formula I) and the carbon atom of the group —CR$^5$(OR$^6$)— in the lower side-chain. In addition, carbon atoms 2, 9 and 11 may also be asymmetrically substituted, so that it is clear that the compounds of the invention may exist in racemic or in optically active form. It is to be understood that the useful biological properties of a racemic compound, comprised of I and its mirror image, may be present to differing extents in the optical isomers, and that this invention relates to racemates and to any optically active form which shows the same useful properties, it being a matter of common general knowledge how the optically active forms may be obtained, and their biological properties determined. It is also to be understood that this invention relates to both C-15 epimers, that is, epimers at the —CR$^3$(OR$^4$)— carbon atom in the lower side chain.

A preferred group of prostane derivatives of the invention having high luteolytic activity comprises compound of the formula I wherein $R^1$ is a carboxy, methoxycarbonyl, ethoxycarbonyl, hydroxymethyl or methoxymethyl radical, $R^2$, $R^3$ and $R^4$, which may be the same or different, are each a hydrogen atom or a methyl radical,

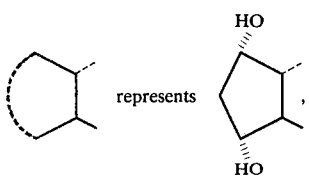 represents 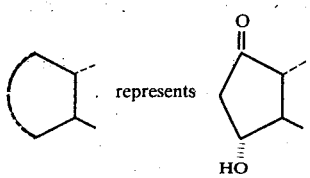 represents

X is a trans-vinylene radical, Y is a methyleneoxy, isopropylideneoxy or methylethylene radical, or a direct bond, n is 1, and R⁵ has the meaning stated above, particularly a phenyl radical, a halogenophenyl radical, for example a chlorophenyl radical, or a halogenoalkylphenyl radical, for example a trifluoromethylphenyl radical, and especially a phenyl, 3-chlorophenyl or 4-trifluoromethylphenyl radical. Preferred compounds in this group are methyl 16-(3-chlorophenoxy) -9α,11α,1-5α-trihydroxy-17,18,19,20-tetranor-4-cis, 13-trans-prostadienoate, methyl 16-(3-chlorophenoxy)-9α,11α,15β-trihydroxy-17,18,19,20-tetranor-4-cis,13-trans-prostadienoate, 16-(3-chlorophenoxy)-9α,11α,15-trihydroxy-17,18,19,20-tetranor-4-cis,13-trans-prostadienoic acid, methyl 16-(3-chlorophenoxy)-9α,11α,15-trihydroxy-16-methyl-18,19,20-trinor-4-cis,13-trans-prostadienoate and methyl 9α,11α,15α-trihydroxy-15-(4-trifluoromethylphenyl)-16,17,18,19,20-pentanor-4-cis,13-trans-prostadienoate.

A preferred group of prostane derivatives of the invention having high activity in the inhibition of blood platelet aggregation comprises those compounds wherein

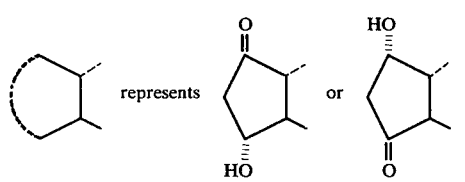 represents or , especially those compounds wherein R¹ is a carboxy or methoxycarbonyl radical, R² and R⁴ are each a hydrogen atom, R³ is a hydrogen atom or a methyl radical, n is 1, X is a trans-vinylene radical, Y is a methyleneoxy or isopropylideneoxy radical, and R⁵ has the meaning stated above, particularly a phenyl radical, a halogenophenyl radical such as a chlorophenyl radical, or a halogenoalkylphenyl radical such as a trifluoromethylphenyl radical, especially a phenyl, 3-chlorophenyl or 4-trifluoromethylphenyl radical. Compounds wherein R⁵ is a 3-chlorophenyl radical are particularly preferred. Preferred individual compounds in this group are methyl 16-(3-chlorophenoxy)-11α,15-dihydroxy-15-methyl-9-oxo-17,18,19,20-tetranor-4-cis,13-trans-prostadienoate, methyl 16-(3-chlorophenoxy)-11α,15-dihydroxy-16-methyl-9-oxo-18,19,20-trinor-4-cis,13-trans-prostadienoate, methyl 16-(3-chlorophenoxy)-9α,15-dihydroxy-15-methyl-11-oxo-17,18,19,20-tetranor-4-cis, 13-trans-prostadienoate and methyl 16-(3-chlorophenoxy)-9α,15-dihydroxy-16-methyl-11-oxo-18,19,20-trinor-4-cis,13-trans-prostadienoate, especially the first two.

Those members of the group of compounds described in the last paragraph wherein also possess high activity as inhibitors of gastric acid production in mammals, and of these methyl 16-(3-chlorophenoxy)-11α,15-dihydroxy-16-methyl-9-oxo-18,19,20-trinor-4-cis,13-trans-prostadienoate is particularly preferred for this purpose.

The novel prostane derivatives of the invention may be manufactured by methods known in themselves for the manufacture of chemically analogous compounds. Thus, the following processes are provided as a further feature of the invention, wherein R¹, R², R³, R⁴, R⁵, n, X and Y have the meanings stated above, unless defined otherwise:

(a) for those compounds wherein

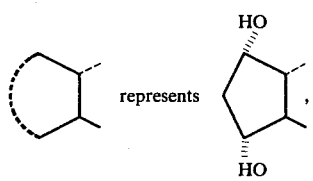 represents , and R³ and R⁴ are each a hydrogen atom, the reduction, for example with sodium borohydride, zinc borohydride, aluminium tri-isopropoxide or di-isobornyloxyaluminium isopropoxide, of an enone of the formula:

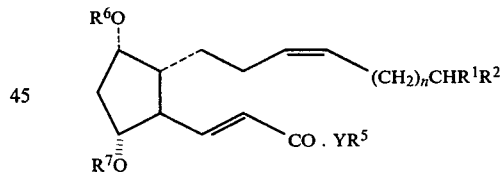

wherein either R¹⁷ is a hydrogen atom and R⁶ is a hydrogen atom or a hydroxy-protecting radical, for example an aroyl radical of up to 15 carbon atoms such as a benzoyl or 4-phenylbenzoyl radical, or R⁶ and R⁷ are each a hydroxy-protecting radical as defined above, whereafter, when either or both of R⁶ and R⁷ is a hydroxy-protecting radical, the product so obtained is hydrolysed, for example under basic conditions;

(b) for those compounds wherein R¹ is an alkoxycarbonyl radical, the reaction of the corresponding prostane derivative of the formula I wherein R¹ is a carboxy radical with a C₁₋₁₁ diazoalkane, or of a salt thereof with a C₁₋₁₁ alkyl halide, for example an alkyl iodide or alkyl bromide;

(c) for those compounds wherein R¹ is a hydroxymethyl radical and

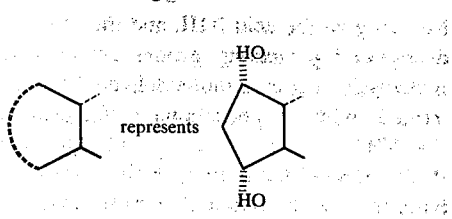 represents the reduction, for example with a complex metal hydride such as lithium aluminium hydride, of the corresponding prostane derivative of the formula I wherein $R^1$ is an alkoxycarbonyl radical;

(d) for those compounds wherein $R^1$ is an alkoxymethyl radical, and

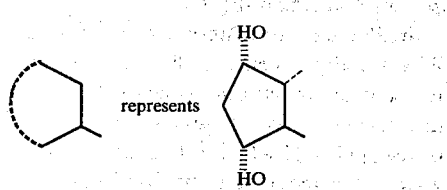 represents the hydrolysis, for example with an acid, such as acetic acid, of a compound of the formula:

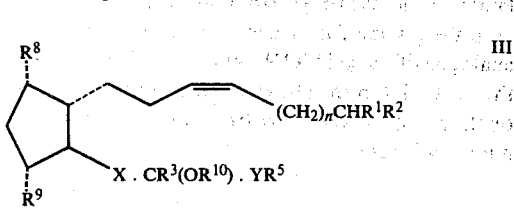

III wherein $R^1$ is a $C_{2-11}$ alkoxymethyl radical, $R^8$ and $R^9$ are each a tetrahydropyran-2-yloxy radical and $R^{10}$ is a tetrahydropyran-2-yl radical or a $C_{1-5}$ alkyl radical;

(e) for those compounds wherein

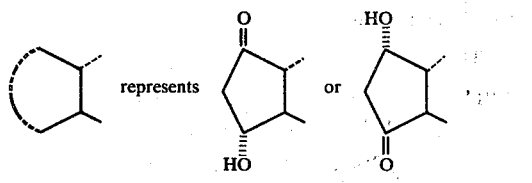 represents and $R^2$ is an alkyl radical, the oxidation, for example with chromium trioxide/pyridine complex, or Jones's reagent (chromic acid in acetone), of a compound of the formula:

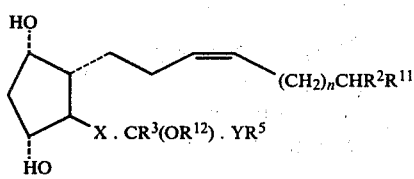

IV wherein $R^{11}$ is a $C_{2-11}$ alkoxycarbonyl radical or a tri($C_{1-5}$-alkyl)silyloxycarbonyl radical, and $R^{12}$ is a $C_{1-5}$ alkyl or tri($C_{1-5}$alkyl)silyl radical, or a tetrahydropyran-2-yl radical, whereafter if necessary the protecting silyl groups are hydrolysed by treating the product so obtained with an acid;

(f) for those compounds wherein $R^4$ is an alkyl radical, the reaction of the corresponding prostane derivative of the formula I wherein $R^4$ is a hydrogen atom with an alkyl halide, for example an alkyl iodide, in the presence of one molecular proportion of a strong base, for example sodium hydride;

(g) for those compound wherein

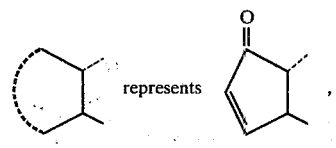 represents , the dehydration of the corresponding prostane derivative of the formula I wherein

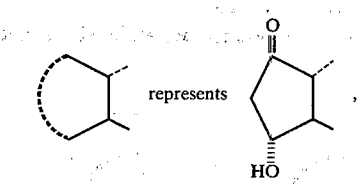 represents , for example with a substituted carbodi-imide in the presence of a copper salt as a catalyst, for example N,N'-dicyclohexyl-carbodi-imide in the presence of cupric chloride;

(h) for those compounds wherein

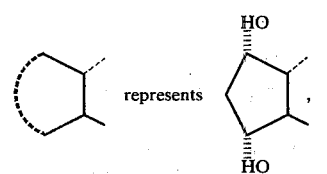 represents , and $R^3$ is an alkyl radical, the hydrolysis, with an acid, of a silyl derivative of the formula:

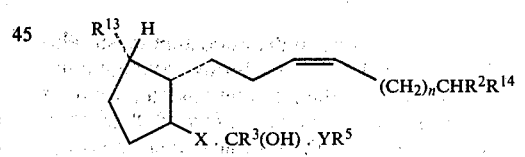

V wherein $R^{13}$ is a tri($C_{1-5}$ alkyl)silyloxy radical, $R^3$ is a $C_{1-5}$ alkyl radical and $R^{14}$ is a tri($C_{1-5}$ alkyl)silyloxycarbonyl, tri($C_{1-5}$ alkyl)silyloxymethyl, $C_{2-12}$ alkoxycarbonyl or $C_{2-12}$ -alkoxymethyl radical;

(i) for those compounds wherein

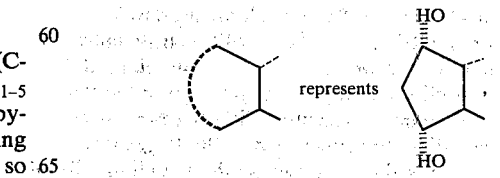 represents , and $R^3$ and $R^4$ are each a hydrogen atom, the hydrolysis, with an acid, of a compound of the formula:

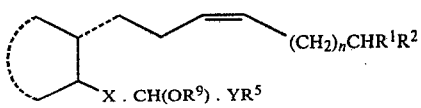

wherein

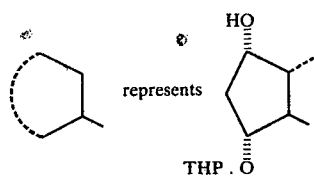

wherein THP is tetrahydropyran-2-yl, and $R^9$ has the meaning defined above; or (j) for those compounds wherein $R^1$ is a carboxy radical, and

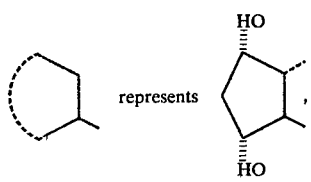

the reaction of a lactol of the formula:

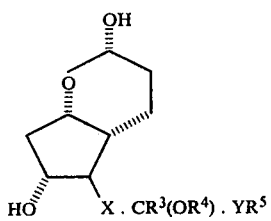

with a (3-carboxypropyl)triphenylphosphonium salt of the formula $Ph_3P^+.(CH_2)_2CHR^2.COOH.Z^-$, wherein $Z^-$ is an anion, for example bromide, in the presence of a strong base.

In process (a), it is to be understood that when aluminium tri-isopropoxide or di-isobornyloxyaluminium isopropoxide is used as the reducing agent, there is obtained a prostane derivative of the formula I wherein X is a trans-vinylene radical, and that when a borohydride reducing agent is used, especially sodium borohydride, there is obtained a mixture of the prostane derivative of the formula I wherein X is a trans-vinylene radical, and the corresponding derivative wherein X is an ethylene radical, from which mixture either component may be isolated by conventional means, for example chromatography.

A starting material of the formula II may be obtained by reacting the known 4β-dimethoxymethyl-2,3,3αβ,-6αβ-tetrahydro-2-hydroxy-5α-(tetrahydropyran-2-yloxy)cyclopenteno[b]-furan VIII with methylenetriphenylphosphorane $(Ph_3P:CH_2)$ to give an olefin IX which is treated with 2,3-dihydropyran to give the bis-ether X. The bis-ether X is reacted with diborane in the presence of alkaline hydrogen peroxide to give the alcohol XI, which is then oxidised with chromium trioxide/pyridine to the aldehyde XII. The aldehyde XII is treated with a (3-carboxypropyl)triphenylphosphonium bromide derivative in the presence of a strong base to give the acid XIII, and the acetal and tetrahydropyranyl protecting groups are removed by acid hydrolysis to give a diol-aldehyde XIV which is then treated with a phosphonate $(C_{1-3}alkoxy)_2PO.CH_2.CO.YR^5$ or a phosphonium salt $Ph_3P^+.CH_2.CO.YR^5.Br^-$, in the presence of a strong base, to give the required starting material of the formula II wherein $R^1$ is a carboxy radical, and $R^6$ and $R^7$ are each a hydrogen atom.

Similar starting materials of the formula II wherein $R^1$ is an alkoxycarbonyl radical may be obtained by esterifying the acid XIII in conventional manner, and using the ester in place of the acid XIII in the above described reaction sequence.

Similar starting materials of the formula II wherein $R^1$ is a hydroxymethyl radical may be obtained by lithium aluminium hydride reduction of the ester described immediately above, to give a hydroxymethyl analogue of the acid XIII which is then used in place of the acid XIII in the above described reaction sequence.

Similar starting materials of the formula II wherein $R^1$ is an alkoxymethyl radical may be obtained by alkylation of the hydroxymethyl analogue of the acid XIII described immediately above, to give an alkoxymethyl analogue of the acid XIII, which is then used in place of the acid XIII in the above described reaction sequence, or they may be obtained from a derivative of the formula I wherein

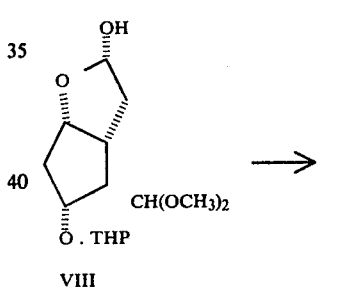

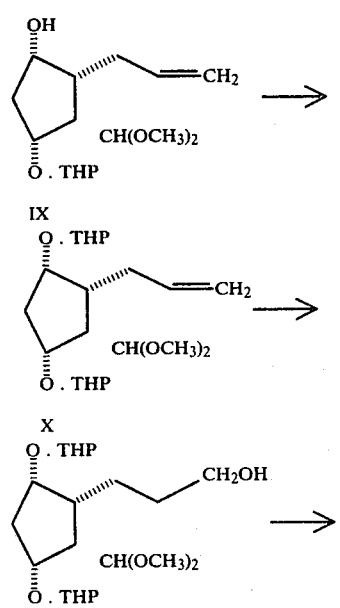

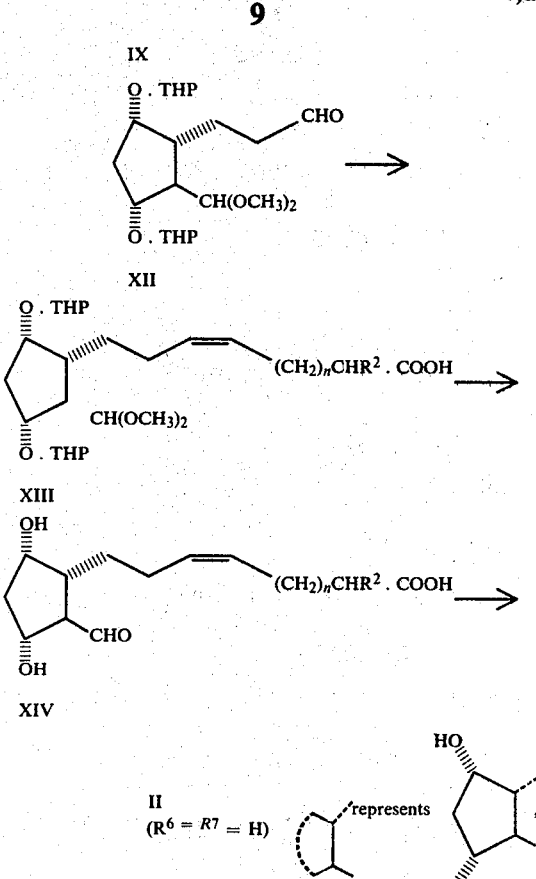

THP = tetrahydropyran-2-yl $R^1$ is an alkoxycarbonyl radical, and $R^4$ is a hydrogen atom, by converting it to a tris(tetrahydropyranyl) derivative, reducing the alkoxycarbonyl radical to a hydroxymethyl radical, alkylating the hydroxymethyl radical with an alkyl halide, and hydrolysing the protecting tetrahydropyranyl radicals.

The starting material of the formula III may be obtained from a prostane derivative of the formula I wherein $R^1$ is an alkoxycarbonyl radical, and

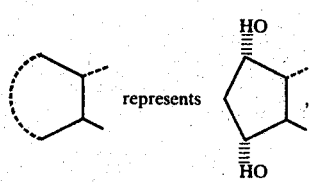

by reaction thereof with an excess of 2,3-dihydropyran, to protect all the hydroxy radicals as tetrahydropyranyl ethers, reduction of the alkoxycarbonyl radical to a hydroxymethyl radical, and alkylation of the hydroxymethyl with an alkyl bromide or alkyl iodide under basic conditions.

The starting material of the formula IV may be obtained by selective silylation of the corresponding prostane derivative of the invention wherein

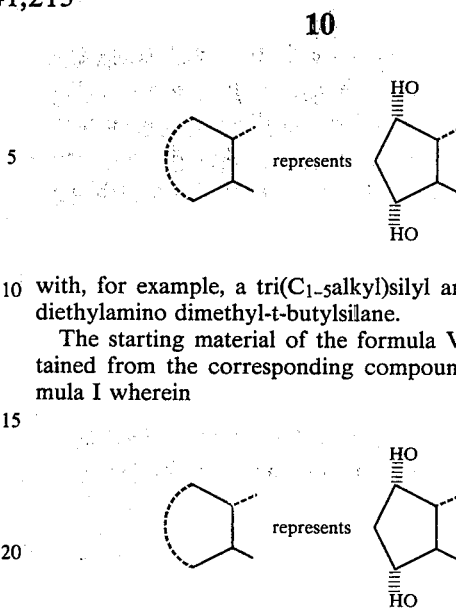

with, for example, a tri($C_{1-5}$alkyl)silyl amide, such as diethylamino dimethyl-t-butylsilane.

The starting material of the formula V may be obtained from the corresponding compound of the formula I wherein and $R^3$ is a hydrogen atom, by selective oxidation with one equivalent of Jones' reagent to give a ketone XV, which is treated with an excess of a silylating agent, for example a tri($C_{1(5}$alkyl)silylamide, to protect the C-9 and C-11 hydroxy radicals, and the carboxy radical if present, giving the silyl derivative XVI. The silyl derivative XVI is then treated with a $C_{1-5}$ alkylmagnesium halide to give the required starting material V.

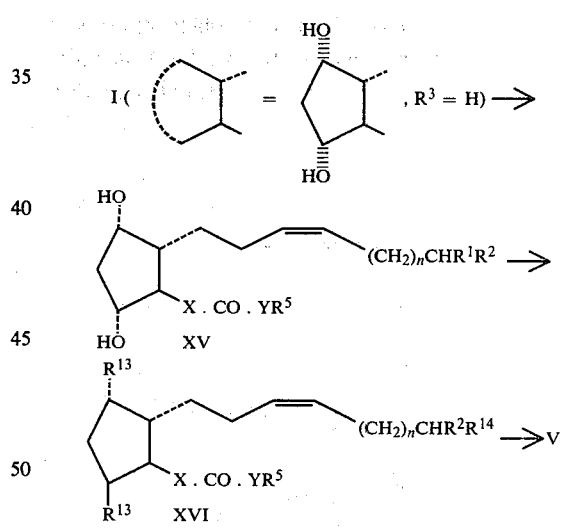

The starting material of the formula VI may be obtained from the olefin IX, by reaction thereof with 4-phenylbenzoyl chloride to give XVII, which is reacted with diborane in the presence of alkaline hydrogen peroxide to give the alcohol XVIII. The alcohol XVIII is oxidised with chromium trioxide/pyridine complex to the aldehyde XIX, which is reacted with a triphenylphosphonium bromide derivative $Ph_3P^+.(CH_2)_nCHR^2.COOH.Br^-$ in the presence of a strong base, to give an acid XX. The acid XX is converted to the ester XXI with diazomethane, and the ester XXI is selectively hydrolysed to the aldehyde XXII. The aldehyde XXII is reacted with a phosphonate $(C_{1-3}$ alkoxy$)_2PO.CH_2.CO.YR^5$ or a phosphonium salt $Ph_3P^+. CH_2.CO.YR^5.Br^-$, in the presence of a strong base, to give an enone XXIII, which is reduced with a borohydride, or a Meerwein-Ponndorf reducing agent, to a diol XXIV. The diol XXIV is reacted with 2,3-dihydropyran to give the protected derivative XXV, which is hydrolysed with a base to give a starting material VI

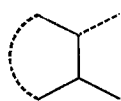  I $R^1$=methoxycarbonyl), which may be oxidised with Jones' reagent to give starting materials VI ($R^1$=methoxycarbonyl,

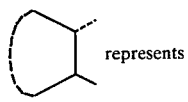 represents

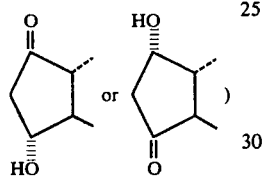

Other starting materials VI may be obtained by conventional chemical manipulation to give starting materials wherein $R^1$ is carboxy, hydroxymethyl or alkoxymethyl.

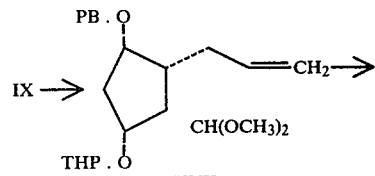

XVII
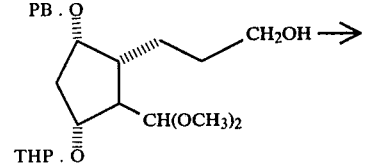

XVIII
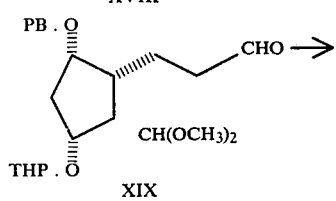

XIX
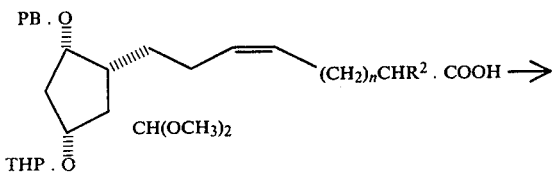

-continued

XX
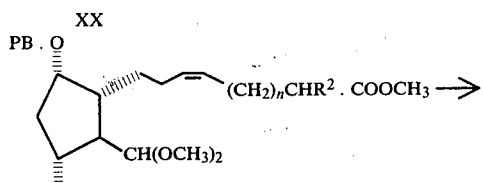

XXI
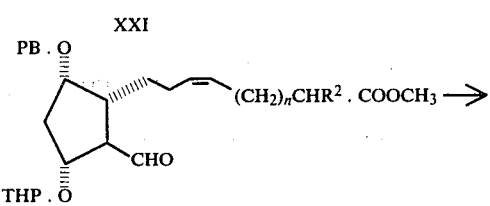

XXII
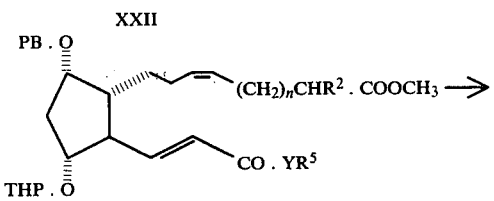

XXIII
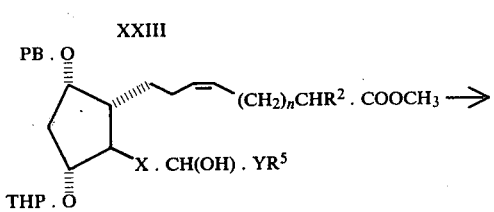

XIV
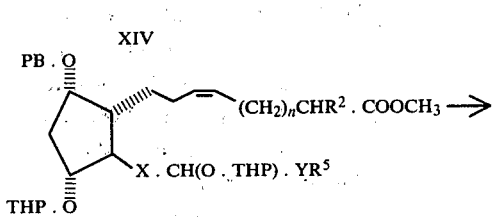

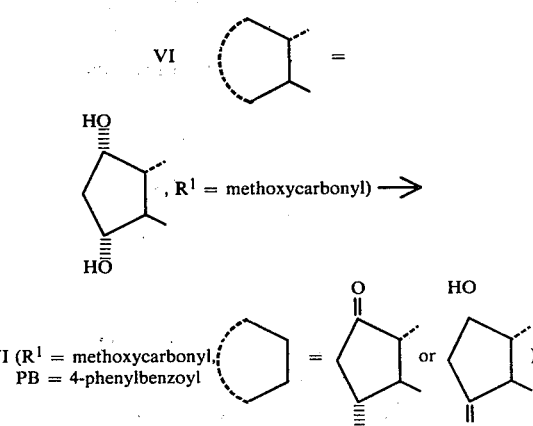

The starting material of the formula VII may be obtained from known bis(tetrahydropyranyl) derivatives XXVI, by reaction thereof with a (methoxymethyl)triphenylphosphonium salt in the presence of a strong base to give an olefin XXVII, which on treatment at pH 2 with hydrochloric acid/potassium chloride buffer in methanol gives a compound XXVIII. Further treatment of the compound XXVIII at pH 1 with hydrochloric acid/potassium chloride buffer in tetrahydrofuran removes the protecting methyl group to give the required lactol starting material VII.

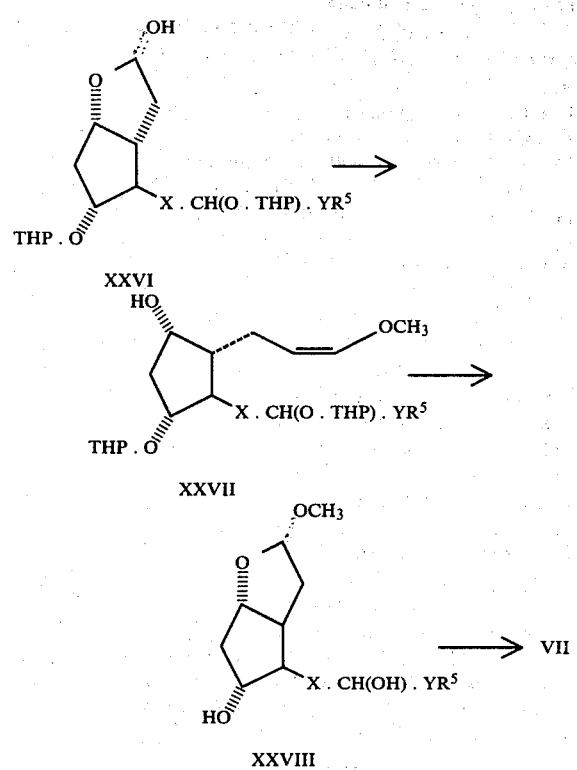

It is to be understood, of course, that an optically active prostane derivative of the invention may be obtained either by resolving the corresponding racemate, or by resolving a suitable starting material or other intermediate in the preparative reaction sequence.

As stated above, the prostane derivatives of the invention possess luteolytic properties, and in particular they are more active as luteolytic agents and less active as smooth muscle stimulants than the naturally occurring prostaglandins. Thus, for example methyl 16-(3-chlorophenoxy)-9α, 11α,15α-trihydroxy-17,18,19,20-tetranor-4-cis, 13-transprostadienoate is approximately 100 times as active as natural prostaglandin F$_2$α as a luteolytic agent in hamsters (subcutaneous dosing) but possesses only approximately one half the smooth muscle stimulant activity.

When a prostane derivative of the invention is to be used for the induction of labour, it is used in the same way as it is known to use the naturally occurring prostaglandin E$_2$, that is by administering a sterile, substantially aqueous solution containing from 0.01 to 10 μg./ml., preferably 0.01 to 1 μg./ml. of the compound, by intravenous infusion, or by transcervical extra-amniotic or intra-amniotic infusion until labour commences. Also, for this purpose, the prostane derivatives of the invention may be used in combination, or concurrently, with a uterine stimulant, for example oxytocin, in the same way as it is known to use the natural prostaglandin in combination, or concurrently, with oxytoxin for the induction of labour.

When a prostane derivative of the invention is to be used for control of the oestrus cycle in animals, for example cattle or horses, it is used in the same way as it is known to use the prostaglandin derivatives known as I.C.I 80996 and I.C.I. 81008 for this purpose. The compounds may be used for this purpose in combination, or concurrently, with a gonadotrophin, for example pregnant mare serum gonadotrophin (PMSG) or human chorionic gonadotrophin (HCG) to hasten the onset of the next cycle.

Also as stated above, certain of the prostane derivatives of the invention are highly active in preventing blood platelet aggregation. Thus, for example, methyl 16-(3-chlorophenoxy)-11α,15-dihydroxy-15-methyl-9-oxo-17,18,19,20-tetranor-4-cis,13-trans-prostadienoate is twice as active as prostaglandin E$_1$ at a concentration of $2 \times 10^{-8}$M, in an in vitro test measuring the inhibition of platelet aggregation caused by adenosine diphosphate in platelet-rich human plasma.

Certain prostane derivatives of the invention are also effective in inhibiting the production of gastric acid in mammals. Thus, for example, methyl 16-(3-chlorophenoxy)-11α,15-dihydroxy-15-methyl-9-oxo-17,18,19,20-tetranor-4-cis, 13-trans-prostadienoate inhibits gastric acid to the extent of 90% in a test in the anaesthetised rat at a subcutaneous dose of 40 μg/kg., i.v.

Thus, according to a further feature of the invention there is provided a pharmaceutical or veterinary composition comprising a prostane derivative of the formula I together with a pharmaceutically or veterinarily acceptable diluent or carrier.

The compositions may be in a form suitable for oral administration, for example tablets or capsules, in a form suitable for inhalation, for example an aerosol or a solution suitable for spraying, in a form suitable for infusion, for example sterile, substantially aqueous, or oily, solutions or suspensions, or in the form of a suppository or pessary, suitable for anal or vaginal use.

The compositions of the invention may be prepared by conventional means, and may contain conventional excipients.

The composition is preferably in the form of a tablet, capsule or a substantially aqueous, sterile solution, and a particular preferred composition is a substantially aqueous, sterile solution containing from 25 to 150 μg/ml., preferably from 25 to 75 μg./ml.

The invention is illustrated, but not limited, by the following Examples. Throughout the example, R$_F$ values refer to silica gel plates supplied commercially by Merck of Darmstadt, and the spots were visualised either by fluoroescence under ultraviolet radiation, by exposure to iodine vapour, or by spraying the plates with a solution of ceric ammonium nitrate in sulphuric acid and heating. Organic solutions were dried with anhydrous magnesium sulphate.

EXAMPLE 1

To a solution of methyl 16-(3-chlorophenoxy)-9α, 11α-dihydroxy-15-oxo-17,18,19,20-tetranor-4-cis,13-transprostadienoate (27 mg.) in dry toluene (1 ml.) was added 1 ml. of a 0.36 M solution of di-isobornyloxyaluminium isopropoxide in toluene. The mixture was stirred at room temperature for 4 hours, and then saturated sodium hydrogen tartrate solution was added. Ethyl acetate (10 ml.) was added, the organic phase separated, washed with a 1:1 mixture of saturated brine and water, and dried. The solvents were evaporated to give a mixture of epimers of methyl 16-(3-chlorophenoxy)-9α,11α,15-trihydroxy-17,18,19,20-tetranor-4-cis,13-trans-prostadienoate. Thin layer chromatography on silica gel using 3% acetic acid in ethyl acetate as the developing solvent, gave the pure isomers, $R_F=0.45$ and 0.5. The n.m.r. spectrum in deuteriated acetone showed the following characteristic bands (δvalues):

6.9–7.4, broad multiplet, 4H, aromatic protons; 5.25–5.75, broad multiplets, 4H, olefinic protons; 3.65, singlet, 3H, methyl ester.

The mass spectrum of the tris(trimethylsilyl) derivative showed (M-3-chlorophenoxymethyl)+ =513.2914 (calculated for $C_{25}H_{49}O_5Si_3=513.2887$). The 9α,11α-dihydroxy compound used as starting material may be obtained as follows:

Finely powdered methyltriphenylphosphonium bromide (6.42 g.) was dried under vacuum for 1 hour and then dissolved in dimethyl sulphoxide (18 ml.), and the solution was cooled to room temperature. To this solution was added 7.5 ml. of a 2M solution of methanesulphinylmethyl sodium in dimethyl sulphoxide, followed by a solution of 4β-dimethoxymethyl-2,3,3aβ,6aβ-tetrahydro-2-hydroxy-5β-(tetrahydropyran-2-yloxy) cyclopenteno [b]furan in a mixture of dimethyl sulphoxide (30 ml.) and toluene (10 ml.). The solution was stirred for 2 hours, and the solvent was removed by evaporation under reduced pressure. The residue was shaken with water (10 ml.) and ether (20 ml.), and the aqueous phase was separated, and re-extracted with ether (6×10 ml.). The extracts were washed with saturated brine and dried, and the solvent was evaporated. The residue was chromatographed on silica gel (100 g.), and elution with 30% ethyl acetate in toluene gave the allyl derivative, 2α-allyl-3β-dimethoxymethyl-4α-(tetrahydropyran-2-yloxy)cyclopentan-1α-ol, $R_F=0.5$ (50% ethyl acetate in toluene).

To a solution of the allyl derivative (1.31 g.) in methylene dichloride (20 ml.), under an atmosphere of nitrogen, were added successively redistilled 2,3-dihydropyran (4 ml.) and a solution of anhydrous toluene-p-sulphonic acid in tetrahydrofuran (0.1 ml. of a 1% solution). After 10 minutes, pyridine (5 drops) was added, followed by ethyl acetate (50 ml.). The solution was washed successively with saturated sodium bicarbonate solution and saturated brine, and was dried. Evaporation of the solvents gave the bis(tetrahydropyranyl ether), 2α-allyl-3β-dimethoxy-methyl-1α,4α-bis(tetrahydropyran-2-yloxy)cyclopentane as a clear oil.

To a solution of the bis(tetrahydropyranyl ether), (192 mg. ), in dry tetrahydrofuran (5 ml.) under an atmosphere of argon at 0° C. was added 1 ml. of a 1M solution of borane in tetrahydrofuran. After 20 minutes, water (1 ml.), 1N sodium hydroxide (1 ml.) and 30% w/v hydrogen peroxide (2.5 ml.) were added successively, and the mixture was stirred at 0° C. for 30 minutes. The reaction mixture was diluted with water (10 ml.) and extracted with ethyl acetate (4×15 ml.). The ethyl acetate extracts were washed successively with dilute sodium sulphite solution, sodium bicarbonate solution and brine, and were then dried, and the solvents were evaporated to give the primary alcohol, 3-8 2β-dimethoxymethyl- 3α,5α-bis(tetrahydropyran-2-yloxy)- cyclopent-1α-yl]propanol, $R_F=0.3$ (50% ethyl acetate in toluene).

A solution of the primary alcohol (200 mg.) in methylene dichloride (5 ml.) was added to a stirred solution of Collins' reagent, prepared from chromium trioxide (400 mg.) and pyridine (0.646 ml.) in methylene dichloride (10 ml.). After 15 minutes at room temperature, the mixture was poured onto a column of "Florisil" (trade mark) magnesium silicate (10 g.), and eluted with methylene dichloride to give the aldehyde, 3-[2β-dimethoxymethyl-3α,5α- bis(tetrahydropyran-2-yloxy) cyclopent-1α-yl]propionaldehyde, as an oil, $R_F=0.6$ (50% ethyl acetate in toluene).

Finely powdered (3-carboxypropyl)triphenyl phosphonium bromide (713 mg.) was heated to 100° C. under vacuum for 1 hour. The evacuated vessel was filled with an atmosphere of dry nitrogen, the solid was dissolved in dimethyl sulphoxide (3 ml.) and the solution was cooled to room temperature. To this solution was added 1.25 ml. of a 2M solution of methanesulphinylmethyl sodium in dimethyl sulphoxide, followed by a solution of the aldehyde described above (200 mg.) in a mixture of dimethyl sulphoxide (5 ml.) and toluene (2 ml.). The solution was stirred for 3 hours, and the solvent was evaporated under reduced pressure at a temperature below 40° C. The residue was shaken with water (3 ml.) and extracted with ether (5=5 ml.), and the extracts were discarded. The aqueous solution was acidified to pH 3–4 with 2 N aqueous oxalic acid, and extracted with a mixture of equal parts of ether and petroleum ether (b.p. 40°–60° C.) (5×6 ml.). The extracts were combined, washed with saturated brine and dried, and evaporation of the solvents gave the acid, 7-[2β-dimethoxymethyl-3α,5α-bis(tetrahydropyran-2-yloxy)cyclopent-1α-yl]hept-4-cis-enoic acid as a clear oil, $R_F=0.3$ (ethyl acetate).

To a solution of the acid (167 mg.) in ether (4 ml.) at 0° C. was added an excess of a solution of diazomethane in ether. After 10 minutes, the solvents were evaporated to give the methyl ester, methyl 7-[2β-dimethoxymethyl-3α,5α-bis(tetrahydropyran-2-yloxy)cyclopent-1α-yl]hept-4-cis-enoate, as a clear oil, $R_F=0.8$ (ethyl acetate).

To a solution of the methyl ester (110 mg.) in tetrahydrofuran (1 ml.) was added 0.5 N hydrochloric acid (2.3 ml.). After 1½ hours, the reaction mixture was neutralised with 1 N sodium hydroxide solution, and to the neutralised mixture were added successively toluene (5 ml.), dimethyl 2-oxo-3-[(3-chlorophenoxy)propyl]phosphonate (103 mg.) and 1 N sodium hydroxide (0.28 ml.). After 18 hours, the mixture was diluted with ethyl acetate (30 ml.) washed with 50% saturated sodium chloride solution, and dried, and the solvents were evaporated.

The residue was chromatographed on silica (15 g.) eluting with 20% ethyl acetate in toluene to remove by-products, and subsequently with 75% ethyl acetate in toluene to give methyl 9α,11α-dihydroxy-15-oxo-16-(3-chlorophenoxy)-17,18,19,20-tetranor-4-cis,13-trans-prostadienoate, $R_F=0.5$ (ethyl acetate).

EXAMPLE 2

To a solution of methyl 16-(3-chlorophenoxy)-16,16,-dimethyl-15-hydroxy-9α,11α-bis(4-phenylbenzoyloxy)-17,18,19,20- tetranor-4-cis,13-trans-prostadienoate (83 mg.) in methanol (1 ml.) was added potassium carbonate (41 mg.). The mixture was stirred at room temperature for 19 hours, acidified to pH 7 with 1 N aqueous hydrochloric acid, and diluted with ethyl acetate (90 mls.). The mixture was washed with brine, the organic phase was separated and dried, and the solvents were evaporated, to give a mixture of C-15 epimers of methyl 16-(3-chlorophenoxy)-16-methyl-9α,11α,15-trihydroxy-18,19,20-trinor-4-cis,13-trans-prostadienoate. Thin layer chromatography on silica gel plates, supplied commercially by Merck of Darmstadt, using ethyl acetate as the developing solvent, gave the pure isomers $R_F=0.2$ and 0.25. The n.m.r. spectrum in deuterated acetone showed the following characteristic bands ($\delta$ values):

6.9–7.4, broad multiplets, 4 aromatic protons; 5.2–5.8, broad multiplets, 4 olefinic protons; 3.5–4.3, broad multiplets 6H, >CH—O—+ exchangeable protons; 3.62, singlet, 3H, —COOCH$_3$; 1.28 and 1.32, 2 singlets, 6H, 16,16-dimethyl protons.

The mass spectrum of the tris(trimethylsilyl) derivative showed (M-[3-chlorophenyl.OC(CH$_3$)$_2$])$^+$=513.2874 (calculated for C$_{25}$H$_{49}$O$_5$Si$_3$=513.2886).

The 9$\alpha$,11$\alpha$-bis(4-phenylbenzoate) used as starting material was obtained as follows:

To a solution of 7-[2$\beta$-dimethoxymethyl-3$\alpha$,5$\alpha$-bis-(tetrahydropyran-2-yloxy)cyclopent-1$\alpha$-yl]hept-4-cis-enoic acid (prepared as described in Example 1) (2.35 g.) in methanol (50 ml.) was added a solution of anhydrous toluene-p-sulphonic acid in tetrahydrofuran (50 ml. of a 0.1 M solution). After 27 hours, pyridine (0.25 ml.) was added, and evaporation of the solvent gave the dihydroxy-ester, methyl 7-(2$\beta$-dimethoxymethyl-3$\alpha$,5$\alpha$-dihydroxycyclopent-1$\alpha$-yl)hept-4-cis-enoate, $R_F=0.35$ (ethyl acetate). The n.m.r. spectrum in deuterochloroform showed the following characteristic bands ($\delta$ values):

5.3–5.7, broad multiplet, 2 olefinic protons; 4.1–4.3, broad multiplet, 3H, >CH—O— protons; 3.65, singlet, 3H, —COOCH$_3$; 3.40, 2 singlets, 6H, methoxy protons.

To a solution of the dihydroxy ester (1.201 g.) in dry pyridine (19 ml.) was added 4-phenylbenzoyl chloride (2.47 g.). After 16 hours, water (1 ml.) was added, and the pyridine was evaporated to give methyl 7-[2$\beta$-dimethoxymethyl-3$\alpha$,5$\alpha$-bis(4-phenylbenzoyloxy)cyclopent-1$\alpha$-yl]hept-4-cis-enoate, $R_F=0.40$ (20% v/v ethyl acetate in toluene).

To a solution of the bis(4-phenylbenzoate) (1.082 g.) in a mixture of acetone (40 ml.) and water (16 ml.) was added toluene-p-sulphonic acid (304 mg.). The mixture was heated under reflux in an atmosphere of argon for 3 hours, and then neutralised with sodium bicarbonate. After evaporation of the solvents, the residue was extracted with ethyl acetate (3×30 ml.). The extracts were combined, washed with a 1:1 v/v mixture of saturated brine and water, and were then dried. Evaporation of the ethyl acetate gave methyl 7-[2$\beta$-formyl-3$\alpha$,5$\alpha$-bis(4-phenylbenzoyloxy)cyclopent-1$\alpha$-yl]-hept-4-cis-enoate, $R_F=0.40$ (20% v/v ethyl acetate in toluene). The n.m.r. spectrum in deuteroacetone showed the following characteristic bands ($\delta$ values):

10.1, doublet, 1H, —CHO; 7.2–8.2, broad multiplets, 18H, phenylbenzoate protons; 5.15–5.75, broad multiplets, 4H, olefinic and >CH—O— protons; 3.5, singlet, 3H, —COOCH$_3$.

Dimethyl 3-(3-chlorophenoxy)-3-methyl-2-oxobutylphosphonate (308 mg) and methyl 7-[2$\alpha$-formyl-3$\alpha$,5$\alpha$-bis(4-phenylbenzoyloxy)cyclopent-1$\alpha$-yl]hept-4-cis-enoate (378 mg.) were dissolved in a mixture of toluene (10.8 ml.) and t-butanol (1.2 ml.). Aqueous 1 M sodium hydroxide solution (0.90 ml.) was added, and the two-phase mixture was stirred vigorously for 18 hours. The organic phase was separated, washed with brine and dried, and the solvent was evaporated. The residue was chromatographed on silica using ethyl acetate/toluene mixtures to elute the enone, methyl 16-(3-chlorophenoxy)-16-methyl-15-oxo-9$\alpha$,11$\alpha$-bis(4-phenylbenzoyloxy)-18,19,20-trinor-4-cis,14-trans-prostadienoate, $R_F=0.25$ (10% v/v ethyl acetate in toluene).

To a solution of the enone (404 mg.) in dry toluene (2 mls.) was added 8.15 ml. of a 0.36 M solution of di-isobornyloxy-aluminium isopropoxide in toluene. The mixture was stirred at room temperature for 4 hours, then saturated sodium hydrogen tartrate solution was added. The mixture was extracted with ethyl acetate (90 ml.), the organic phase separated, washed with brine and dried, and the solvents were evaporated to give a mixture of C-15 epimers of methyl 16-(3-chlorophenoxy)-16-methyl-15-hydroxy-9$\alpha$,11$\alpha$-bis(4-phenylbenzoyloxy)-18,19,20-trinor-4-cis,13-trans-prostadienoate, $R_F=0.20$ and 0.25 (15% v/v ethyl acetate in toluene).

EXAMPLE 3

The process described in the first part of Example 2 was repeated, using methyl-15-hydroxy-9$\alpha$,11$\alpha$-di(4-phenylbenzoyloxy)-15-(4-trifluoromethylphenyl)-16,17,18,19,20-pentanor-4-cis,13-trans-prostadienoate as the starting material, to give the separated C-15 epimers of methyl 9$\alpha$,11$\alpha$,15-trihydroxy-15-(4-trifluoromethylphenyl)-16,17,18,19,20-pentanor-4-cis,13-trans-prostadienoate, $R_F=0.2$ and 0.3 (2½% v/v acetic acid/ethyl acetate). The n.m.r. spectrum of each epimer in deuterated acetone showed the following characteristic features ($\delta$ values):

7.6, singlet, 4H, aromatic protons; 5.2–5.8, broad multiplets, 5H, C-15 and 4 olefinic protons; 3.2–4.7, broad multiplets, 5H, >CH—O— and —OH protons; 3.6, singlet, 3H, —COOCH$_3$.

The mass spectrum of the tris(trimethylsilyl)-derivative of the more polar epimer showed M$^+$=658.3108 (calculated for C$_{32}$H$_{53}$F$_3$O$_5$Si$_3$=658.3149).

The bis(4-phenylbenzoate) used as starting material was prepared by the process described in the latter part of Example 2, using the appropriate phosphonate, to give the enone, methyl 15-oxo-9$\alpha$,11$\alpha$-bis(4-phenylbenzoyloxy)-15-(4-trifluoromethylphenoxy)-16,17,18,19,20-pentanor-4-cis, 13-trans-prostadienoate, $R_F=0.30$ (10% v/v ethyl acetate in toluene).

The n.m.r. spectrum in deuterochloroform showed the following characteristic features ($\delta$ values):

7.0–8.3, broad multiplets, 24H, aromatic and trans-olefinic protons; 5.2–5.7, broad multiplets, 4H>CH—O— and cis-olefinic protons; 3.58, singlet, 3H, —COOCH$_3$.

The enone was reduced to the required bis(4-phenylbenzoate) starting material by the process described at the end of Example 2.

EXAMPLE 4

The process described in the first part of Example 2 was repeated, using methyl 16-benzyl-15-hydroxy-9$\alpha$,11$\alpha$-bis(4-phenylbenzoyloxy)-18,19,20-trinor-4-cis,13-trans-prostadienoate as the starting material, to give methyl 16-benzyl-9$\alpha$,11$\alpha$,15-trihydroxy-18,19,20-trinor-4-cis,13-trans-prostadienoate, $R_F=0.20$ and 0.30. The n.m.r. spectrum in deuterated acetone showed the following characteristic bands ($\delta$ values):

7.3, singlet, 5H, aromatic protons; 5.3–5.7, broad multiplets, 4H, olefinic protons; 3.65, singlet, 3H, —COOCH$_3$; 0.7–0.9, double doublet, 3H, C-17 protons. The mass spectrum of the tris(trimethylsilyl) derivative of the more polar epimer showed M$^+$=617.3494 (calculated for C$_{34}$H$_{60}$O$_5$Si$_3$=617.3510). The bis(4-phenylbenzoate) used as starting material was prepared by the process described in the latter part of Example 2, using the appropriate phosphonate to give the enone, methyl 16-benzyl-15-oxo-9$\alpha$,11$\alpha$-bis(4-phenylbenzoyloxy)-

18,19,20-trinor-4-cis, 13-trans-prostadienoate, $R_F=0.25$ (10% v/v ethyl acetate in toluene).

The n.m.r. spectrum in deuterated chloroform showed the following characteristic bands ($\delta$ values):

6.8–8.2, broad multiplets, 24H, C-13 and aromatic protons; 6.22, doublet, 1H, C-14 proton; 5.2–5.6, broad multiplets 4H, cis-olefinic and C9 and C11 protons; 3.6, singlet, 3H, —COOCH$_3$; 1.0–1.1, doublet, 3H, C-17 protons.

EXAMPLE 5

The process described in Example 1 was repeated, using methyl 16-(3-chlorophenoxy)-9α,11α-dihydroxy-15-oxo-17,18,19,20-tetranor-4-cis, 13-trans-2α-homoprostadienoate as the starting material, to give methyl 16-(3-chlorophenoxy)-9α,11α,15-trihydroxy-17,18,19,20-tetranor-4-cis,13-trans-2α-homoprostadienoate, $R_F=0.4$ (3% v/v acetic acid in ethyl acetate). The n.m.r. spectrum in deuterated acetone showed the following characteristic bands ($\delta$ values):

6.9–7.5, broad multiplets, 4 aromatic protons; 5.3–5.8, broad multiplets, 4 olefinic protons; 3.6, singlet, 3H, —COOCH$_3$ The mass spectrum of the tris(trimethylsilyl) derivative showed (M-[3-chlorophenoxymethyl])$^+$ = 527.3033, (calculated for $C_{26}H_{51}O_5Si_3 = 527.3044$)

The 9α,11α-dihydroxy compound used as starting material was prepared by the process described in the second part of Example 1, using (4-carboxybutyl)triphenyl-phosphonium bromide in place of (3-carboxypropyl)triphenylphosphonium bromide, to give methyl 8-[2β-dimethoxymethyl-3α,5α-bis(tetra-hydropyran-2-yloxy)cyclopent-1α-yl]oct-5-cis-enoate, $R_F=0.3$ (ethyl acetate).

The remainder of the process described in the latter part of Example 1 was repeated, using the above described bis(tetrahydropyranyl) derivative, to give the required starting material, methyl 16-(3-chlorophenoxy)-9α,11α-dihydroxy-15-oxo-17,18,19,20-tetranor-4-cis,13-trans-2α-homoprostadienoate, $R_F=0.5$ (10% v/v methanol in ethyl acetate).

EXAMPLE 6

Methyl 16-(3-chlorophenoxy)-9α,11α,15-trihydroxy-17,18,19,20-tetranor-4-cis,13-trans-prostadienoate (22 mg.) was stirred at room temperature under argon in a mixture of methanol (2.5 ml.) and water (0.5 ml.) with 1 M potassium hydroxide in methanol (0.5 ml.) for 16 hours. Glacial acetic acid was added to adjust the pH of the solution to 7, and the solvents were evaporated under reduced pressure. The residue was acidified to pH 3-4 with oxalic acid, and was extracted with ethyl acetate (3×15 mls.). The extracts were washed with brine and dried, and the solvents were evaporated, to give a mixture of C-15 epimers of 16-(3-chlorophenoxy)-9α,11α,15-trihydroxy-17,18,19,20-tetranor-4-cis,13-trans-prostadienoic acid. The mixed epimers were separated by thin-layer chromatography using 3% v/v acetic acid in ethyl acetate, $R_F=0.10$ and 0.15. The n.m.r. spectrum, in deuterated acetone showed the following characteristic bands ($\delta$ values):

6.9–7.5, broad multiplets, 4 aromatic protons; 5.3–5.8, broad multiplets, 4 olefinic protons; 3.8–5.0, broad multiplets, 9H,C-9,11,15 and 16, and OH protons.

The mass spectrum of the tetra(trimethylsilyl) derivative of the more polar epimer showed (M-[3-chlorophenoxy-methyl])$^+$ = 571.3111, (calculated for $C_{27}H_{55}O_5Si_4 = 571.3127$).

EXAMPLE 7

The process described in Example 6 was repeated, using methyl 16-benzyl-9α,11α,15-trihydroxy-18,19,20-trinor-4-cis,13-trans-prostadienoate as the starting material, to give 16-benzyl-9α,11α,15-trihydroxy-18,19,20-trinor-4-cis, 13-trans-prostadienoic acid, $R_F=0.20$ and 0.25 (2½% v/v acetic acid in ethyl acetate). The n.m.r. spectrum in deuterated acetone showed the following characteristic bands ($\delta$ values):

7.1–7.4, multiplet, 5H, aromatic protons, 5.2–5.6, broad multiplets, 4H, olefinic protons, 3.7–4.6, broad multiplets, 7H, C-9,11 and 15, and OH protons; 2.8–3.1, broad multiplets, 1H, C-16 proton; 0.75–0.9, double doublet, 3H, 17-methyl.

The mass spectrum of the tetra(trimethylsilyl) derivative showed M$^+$ = 690.3986, (calculated for $C_{36}H_{66}O_5Si_4 = 690.3929$).

EXAMPLE 8

The process described in the first part of Example 2 was repeated, using methyl 16-(3-chlorophenoxy)-15-hydroxy-15-methyl-9α,11α-bis(4-phenyl-benzoyloxy)-17,18,19,20-tetranor-4-cis,13-trans-prostadienoate as the starting material, to give the mixed C-15 epimers of methyl 16-(3-chlorophenoxy)-15-methyl-9α,11α,15-trihydroxy-17,18,19,20-tetranor-4-cis,13-trans-prostadienoate, $R_F=0.20$ (3% v/v acetic acid in ethyl acetate). The n.m.r. spectrum in deuterated acetone showed the following characteristic bands ($\delta$ values):

6.8–7.3, broad multiplets, 4 aromatic protons; 5.2–5.8, broad multiplets, 4 olefinic protons; 3.3–4.3, broad multiplets, methyl ester, C-9,11 and 16 and OH protons; 1.35, doublet, 3H, 15-methyl protons.

The mass spectrum of the tris(trimethylsilyl) derivative showed (M-CH$_3$)$^+$ = 653.2930 (calculated for $C_{32}H_{54}ClO_6Si_3 = 653.2913$).

The 9α,11α-bis(4-phenylbenzoate) used as starting material may be obtained as follows:

To a solution of methyl 16-(3-chlorophenoxy-15-oxo-9α,11α-bis(4-phenylbenzoyloxy)-17,18,19,20-tetranor-4-cis,13-trans-prostadienoate (244 mg.) (prepared as in Example 2) in tetrahydrofuran (9.2 ml.) at −78° C. was added a 3.4 M solution of methyl magnesium bromide in ether (0.90 ml.). After 20 minutes, saturated aqueous ammonium chloride (10 ml.) was added, followed by ethyl acetate (90 ml.). The solution was washed with brine, and was dried, and evaporation of the solvents gave methyl 16-(3-chlorophenoxy)-15-hydroxy-15-methyl-9α,11α-bis(4-phenylbenzoyloxy)-17,18,19,20-tetranor-4-cis,13-trans-prostadienoate, $R_F=0.25$ (20% v/v ethyl acetate in toluene).

EXAMPLE 9

To a solution of methyl 16-benzyl-9α,11α,15-trihydroxy-18,19,20-trinor-4-cis,13-trans-prostadienoate (21 mg.) in ether (6 ml.) was added lithium aluminium hydride (38 mg.). The mixture was stirred at room temperature for ½ hour, the excess of hydride was destroyed by the addition of water (1 ml.), and the mixture was extracted with ethyl acetate. The extracts were dried, and the solvent was evaporated to give 16-benzyl-18,19,20-trinor-4-cis,13-trans-prostadien-1,9α,11α,15-tetraol, $R_F=0.30$ and 0.35 (10% v/v methanol in ethyl acetate). The n.m.r. spectrum in deuterated acetone showed the following characteristic bands ($\delta$ values):

7-15, singlet, 5H aromatic protons; 5.2-5.7, broad multiplets, 4H, olefinic protons; 3.3-4.3, broad multiplets, 9H, C-1,9,11 and 15, and OH protons; 2.7-3.1, broad multiplets, 3H, Ph-CH$_2$-CH<; 0.75-0.95, double doublet, 3H, C-17 methyl protons.

The mass spectrum of the tetra(trimethylsilyl) derivative showed M$^+$=676.4194 (calculated for C$_{36}$H$_{68}$O$_4$-Si$_4$=676.4229).

EXAMPLE 10

A solution of a mixture of methyl 16-(3-chlorophenoxy)-11α-hydroxy-9-oxo-15-(tetrahydropyran-2-yloxy)-17,18,19,20-tetranor-4-cis,13-trans-prostadienoate and methyl 16-(3-chlorophenoxy)-9α-hydroxy-11-oxo-15-(tetrahydropyran-2-yloxy)-17,18,19,20-tetranor-4-cis,13-trans-prostadienoate (53 mg.) in 2 ml. of a 2:1 v/v mixture of acetic acid and water, and 0.5 ml. of tetrahydrofuran was stirred at 50° C. for 6 hours. The solvents were evaporated and the residue was chromatographed on silica gel plates using ethyl acetate as the developing solvent, to give:

methyl 16-(3-chlorophenoxy)-11α,15-dihydroxy-9-oxo-17,18,19,20-tetranor-4-cis,13-trans-prostadienoate, R$_F$=0.2 and 0.3 (ethyl acetate), n.m.r. spectrum in deuterated acetone:

6.8-7.4δ, broad multiplet, 4 aromatic protons; 5.3-5.9, broad multiplets, 4 olefinic protons; 3.9-4.7, broad multiplets, 6H, C-11,15 and 16, and OH protons; 3.58, singlet, —COOCH$_3$;

Mass spectrum of the 9-methoxime-bis(trimethylsilyl) derivative M$^+$=609.2699, (calculated for C$_{30}$H$_{48}$ClNO$_6$Si$_2$=609.2706);

Methyl 16-(3-chlorophenoxy)-9α,15-dihydroxy-11-oxo-17,18,19,20-tetranor-4-cis,13-trans-prostadienoate, R$_F$=0.19 and 0.21 (50% v/v ethyl acetate in toluene), n.m.r. spectrum in deuterated acetone:

6.8-7.4δ, broad multiplets, 4 aromatic protons; 5.3-5.8, broad multiplets, 4 olefinic protons; 3.8-4.6, broad multiplets, 6H, C-9,15 and 16, and OH protons; 3.60, singlet, 3H, —COOCH$_3$;

Mass spectrum of the 11-methoxime-bis(trimethylsilyl) derivative, M$^+$=609.2651, (calculated for C$_{30}$H$_{48}$ClNO$_6$Si$_2$=609.2606) The mixture of 9-oxo- and 11-oxo-tetrahydropyranyl derivatives used as the starting material for the above process was obtained as follows:

To a solution of methyl 16-(3-chlorophenoxy)-15-hydroxy-9α,11α-bis(4-phenylbenzoyloxy)-17,18,19,20-tetranor-4-cis,13-trans-prostadienoate (199 mg.) in methylene dichloride (2.5 ml.), under an atmosphere of argon, were added successively redistilled 2,3-dihydropyran (0.23 ml.) and a solution of anhydrous toluene-p-sulphonic acid in tetrahydrofuran (0.1 ml. of a 0.1 M solution). After 10 minutes, pyridine (3 drops) was added, followed by ethyl acetate (90 ml.). The solution was washed successively with saturated sodium bicarbonate solution and brine, and was dried. Evaporation of the solvents gave the corresponding tetrahydropyranyl ether as a clear oil, R$_F$=0.20 (10% v/v ethyl acetate in toluene).

The process described in the first part of Example 2 was repeated, using the above-described tetrahydropyranyl ether as starting material, to give methyl 16-(3-chloro-phenoxy)-9α,11α-dihydroxy-15-(tetrahydropyran-2-yloxy)-17,18,19,20-tetranor-4-cis,13-trans-prostadienoate, R$_F$=0.30 (ethyl acetate).

To a solution of methyl 16-(3-chlorophenoxy)-9α,1-1α-dihydroxy-15-(tetrahydropyran-2-yloxy)-17,18,19,20-tetranor-4-cis,13-trans-prostadienoate (106 mg.) in acetone (40ml.) at −40° C., was added Jones' reagent (chromic acid in acetone) (50 μl., 8 N). After 50 minutes, isopropanol (1 ml.) was added and the solution was neutralised to pH 7 with saturated aqueous sodium bicarbonate. The solvent was evaporated, and the residue was dissolved in ethyl acetate (40 ml.). The solution was washed with brine and dired, and evaporation of the solvents gave the required mixture of the 9-oxo-tetrahydropyranyl ether, R$_F$=0.15 (50% v/v ethyl acetate in toluene) and the 11-oxo-tetrahydropyranyl ether, R$_F$=0.25 (50% v/v ethyl acetate in toluene).

EXAMPLE 11

The process described in Example 10 was repeated, using a mixture of methyl 16-(3-chlorophenoxy)-11α-hydroxy-16-methyl-9-oxo-15-(tetrahydropyran-2-yloxy)-18,19,20-trinor-4-cis,13-trans-prostadienoate and methyl 16-(3-chlorophenoxy)-9α-hydroxy-16-methyl-11-oxo-15-(tetrahydropyran-2-yloxy)-18,19,20-trinor-4-cis,13-trans-prostadienoate as the starting material, to give:

methyl 16-(3-chlorophenoxy)-11α,15-dihydroxy-16-methyl-9-oxo-18,19,20-trinor-4-cis,13-trans-prostadienoate, R$_F$=0.3 and 0.4 (ethyl acetate), n.m.r. spectrum in deuterated acetone:

6.9-7.4δ, broad multiplets, 4 aromatic protons; 5.3-5.9, broad multiplets, 4 olefinic protons; 3.9-4.3, broad multiplets, 4H, C-11 and 15, and OH protons; 3.58, singlet, 3H, —COOCH$_3$; 1.24 and 1.28, 2 singlets, 6H, 16,16,-dimethyl.

Mass spectrum of bis(trimethylsilyl) derivative showed (M-CH$_3$)$^+$=593.2496 (calculated for C$_{30}$H$_{46}$ClO$_6$-Si$_2$=593.2522);

and methyl 16-(3-chlorophenoxy)-9α,15-dihydroxy-16-methyl-11-oxo-18,19,20-trinor-4-cis,13-trans-prostadienoate, R$_F$=0.20 and 0.25 (50% v/v ethyl acetate in toluene), n.m.r. spectrum in deuterated acetone:

6.9-7.4δ, broad multiplets, aromatic protons; 5.3-5.9, broad multiplets, olefinic protons; 3.9-4.6, broad multiplets, C-9 and 15, and OH protons; 3.58, singlet, 3H, —COOCH$_3$; 1.22 and 1.28, 2 singlets, 6H, 16,16-dimethyl;

Mass spectrum of 11-methoxime-bis(trimethylsilyl) derivative showed (M-CH$_3$)$^+$=622.2734 (calculated for C$_{31}$H$_{49}$ClNO$_6$Si$_2$=622.2787).

The mixture of 9-oxo- and 11-oxo-tetrahydropyranyl derivatives used as starting material was prepared by the process described in the latter part of Example 10, starting from the corresponding 16-methyl-trinor compound, via methyl 16-(3-chlorophenoxy)-16-methyl-9α,11α-bis(4-phenylbenzoyloxy)-15-(tetrahydropyran-2-yloxy)-18,19,20-trinor-4-cis,13-trans-prostadienoate, R$_F$=0.20 and 0.30 (10% v/v ethyl acetate in toluene), and methyl 16-(3-chlorophenoxy)-9α,11α-dihydroxy-16-methyl-15-(tetrahydropyran-2-yloxy)-18,19,20-trinor-4-cis,13-trans-prostadienoate, R$_F$=0.30 (ethyl acetate).

EXAMPLE 12

The oxidation process using Jones's reagent, described in the last part of Example 10, was repeated using methyl 16-(3-chlorophenoxy)-9α,11α,15-trihydroxy-15-methyl-17,18,19,20-tetranor-4-cis,13-trans-prostadienoate as the starting material, to give:

methyl 16-(3-chlorophenoxy)-11α, 15-dihydroxy-15-methyl-9-oxo-17,18,19,20-tetranor-4-cis,13-trans-prostadienoate, $R_F=0.25$ (ethyl acetate), n.m.r. spectrum in deuterated acetone:

6.8–7.4, broad multiplets, 4 aromatic protons; 5.2–5.9, broad multiplets, 4 olefinic protons; 3.8–4.3, broad multiplets, 5H, C-11 and 16, and OH protons; 3.58, singlet, 3H, —COOCH$_3$; 1.38, 2 singlets, 3H, 15-methyl, mass spectrum of the 9-methoxime-bis(trimethylsilyl) derivative, showed M$^+$=623.2864, (calculated for C$_{31}$H$_{50}$ClNO$_6$Si$_2$=623.2862);

and methyl 16-(3-chlorophenoxy)-9α,15-dihydroxy-15-methyl-11-oxo-17,18,19,20-tetranor-4-cis,13-trans-prostadienoate, $R_F=0.45$ (ethyl acetate), n.m.r. spectrum in deuterated acetone:

6.8–7.4, broad multiplets, 4 aromatic protons; 5.3–5.9, broad multiplets, 4 olefinic protons; 3.8–4.6, broad multiplets, 5H, C-9 and 16, and OH protons, 3.58, singlet, 3H, —COOCH$_3$; 1.35, singlet, 3H, 15-methyl, mass spectrum of the 11-methoxime-bis(trimethylsilyl) derivative showed (M-CH$_3$)$^+$=608.2650, (calculated for C$_{30}$H$_{47}$ClNO$_6$Si$_2$=608.2627).

The starting material for the above process was obtained by repeating the first part of Example 2 using methyl 16-(3-chlorophenoxy)-15-hydroxy-15-methyl-9α,11α-bis(4-phenylbenzoyloxy)-17,18,19,20-tetranor-4-cis,13-trans-prostadienoate as the starting material, to give the required methyl 16-(3-chlorophenoxy)-9α,11α,15-trihydroxy-15-methyl-17,18,19,20-tetranor-4-cis,13-trans-prostadienoate, $R_F=0.20$ (3% v/v acetic acid in ethyl acetate).

EXAMPLE 13

The process described in the first part of Example 2 was repeated, using a mixture of methyl 16-benzyl-15-hydroxy-9α,11α-bis(4-phenylbenzoyloxy)-18,19,20-trinor-4-cis-prostenoate and methyl 16-benzyl-15-hydroxy-9α,11α-bis(4-phenylbenzoyloxy)-18,19,20-trinor-4-cis,13-trans-prostadienoate as the starting material, to give, after purification on thin layer chromatography plates impregnated with silver nitrate, using 5% v/v acetic acid in ethyl acetate as eluting solvent, methyl 16-benzyl-9α,11α,15-trihydroxy-18,19,20-trinor-4-cis-prostenoate, $R_F=0.40$ (5% v/v acetic acid in ethyl acetate). The n.m.r. spectrum in deuterated acetone showed the following characteristic bands (δ values):

7.30, singlet, 5H, aromatic protons; 5.3–5.7, broad multiplet, 2H, olefinic protons; 3.3–4.3, broad multiplets, 9H, C-9,11 and 15, and OH protons+methyl ester; 0.76–0.90, double doublet, 3H, methyl.

The mass spectrum of the tris(trimethylsilyl) derivative showed M$^+$=619.3662, (calculated for C$_{34}$H$_{62}$O$_5$Si$_3$=619.3666). The mixture of enol and saturated alcohol used as starting material may be obtained as follows:

To a solution of methyl 16-benzyl-15-oxo-9α,11α-bis(4-phenylbenzoyloxy)-18,19,20-trinor-4-cis,13-trans-prostadienoate (60 mg.) in 1,2-dimethoxyethane (1 ml.) was added sodium borohydride (25 mg.). After 30 minutes at room temperature, the solution was adjusted to pH 4 with saturated sodium hydrogen tartrate solution and extracted with ethyl acetate (3×10 ml.). The extracts were combined, washed with saturated sodium hydrogen carbonate and then with saturated brine and dried. Evaporation of the solvents gave the required mixture of methyl 16-benzyl-15-hydroxy-9α,11α-bis(4-phenylbenzoyloxy)-18,19,20-trinor-4-cis-prostenoate and methyl 16-benzyl-15-hydroxy-9α,11α-bis(4-phenylbenzoyloxy)-18,19,20-trinor-4-cis,13-trans-prostadienoate, $R_F$ 0.45 (25% v/v ethyl acetate in toluene).

EXAMPLE 14

A solution of 16-benzyl-1-methoxy-9α,11α,15-tris(tetrahydropyran-2-yloxy)-18,19,20-trinor-4-cis,13-trans-prostadiene (43 mg.) in a 2:1 v/v mixture of acetic acid and water (3 ml.) was stirred at 45° C. for 3 hours. The solvents were evaporated, and the residue was chromatographed on thin-layer chromatography plates using 2½% v/v acetic acid in ethyl acetate as the developing solvent to give 16-benzyl-1-methoxy-18,19,20-trinor-4-cis,13-trans-prostadien-9α,11α,15-triol as a clear oil, $R_F=0.30$ (2½% v/v acetic acid in ethyl acetate). The n.m.r. spectrum showed the following characteristic bands (δ values):

7.1–7.3, doublet, 5H, aromatic protons; 5.2–5.6, broad multiplets, 4H, olefinic protons; 3.1–4.3, broad multiplets, 11H, C-1,9,11 and 15, and OH protons, and 1-methoxy; 0.75–0.9, double doublet, methyl.

The mass spectrum of the tris(trimethylsilyl) derivative showed M$^+$=618.3955 (calculated for C$_{34}$H$_{62}$O$_4$Si$_3$=618.3921).

The tris(tetrahydropyranyl ether) used as starting material may be prepared as follows:

To a solution of the more polar C-15 epimer of methyl 16-benzyl-9α,11α,15-trihydroxy-18,19,20-trinor-4-cis,13-trans-prostadienoate (33 mg.) in methylene dichloride (3 ml.), under an atmosphere of nitrogen, were added successively redistilled 2,3-dihydropyran (207 μl.) and a solution of anhydrous toluene-p-sulphonic acid in tetrahydrofuran (57 μl. of a 1% w/v solution). After 10 minutes, pyridine (3 drops) was added, followed by ethyl acetate (50 ml.). The solution was washed successively with saturated sodium bicarbonate solution and saturated brine, and was dried. Evaporation of the solvents gave the tris(tetrahydropyranyl ether) as a clear oil, $R_F=0.7$ (50% v/v ethyl acetate in toluene).

A solution of the tris(tetrahydropyranyl ether), (50 mg.) in dry ether (3 ml.) was added to a suspension of lithium aluminium hydride (57 mg.) in ether (5 ml.). The mixture was stirred at room temperature for 2 hours, the excess of hydride was destroyed by the addition of water (1 ml.) and the mixture was extracted with ethyl acetate to give the 1-alcohol, 16-benzyl-9α,11α,15-tris(tetrahydropyran-2-yloxy)-18,19,20-trinor-4-cis,13-trans-prostadien-1-ol, $R_F=0.3$ (50% v/v ethyl acetate in toluene).

To a solution of 1-alcohol (39 mg.) in dimethoxyethane (1 ml.) were added successively methyl iodide (0.5 ml.) and sodium hydride (4 mg. of a 80% w/v suspension in oil). The mixture was stirred at room temperature for 18 hours, the solvents were removed under reduced pressure, and the residue was shaken with a mixture of ethyl acetate (10 mls.) and water (2 mls.). The organic phase was separated and dried, and the solvent was evaporated to give the required tris(tetrahydropyranyl ether), $R_F=0.6$ (ethyl acetate).

EXAMPLE 15

| | % w/v |
|---|---|
| 16-(3-Chlorophenoxy)-9α,11α,15α-trihydroxy-17,18,19,20-tetranor-4-cis,13-trans-prostadienoic acid | 0.003 |
| Sodium phosphate B.P. | 2.90 |
| Sodium acid phosphate BP | 0.30 |
| Water for injection | to 100 |

The sodium phosphate B.P. was dissolved in about 80% of the water, followed by the prostadienoic acid derivative, and when dissolved, the sodium acid phosphate B.P. The solution was made up to volume with water for injection, and the pH was checked to be between 6.7 and 7.7. The solution was filtered to remove particulate matter, sterilised by filtration, and filled into pre-sterilised neutral glass ampoules under aseptic conditions. Immediately before use, the contents of an ampoule are diluted in sodium chloride B.P. for administration by intravenous infusion.

The prostadienoic acid derivative may of course, be replaced by an equivalent amount of another prostanoic acid derivative of the invention.

EXAMPLE 16

The process described in Example 14 was repeated, omitting the sodium phosphate B.P. and sodium acid phosphate B.P., to give ampoules containing a sterile aqueous solution of 16-(3-chlorophenoxy)-9α,11α,15-trihydroxy-17,18,19,20-tetranor-4-cis,13-trans-prostadienoic acid, which are used in the manner described in Example 15.

The prostadienoic acid derivative may be replaced by an equivalent amount of another prostadienoic acid of the invention, to give other sterile aqueous solutions.

What we claim is:

1. A prostane derivative of the formula:

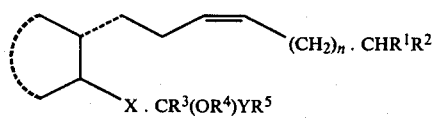

wherein

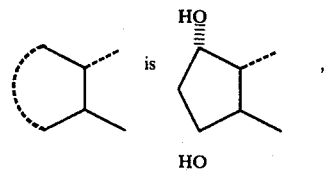

$R^1$ is carboxy or $C_{2-12}$ alkoxycarbonyl, $R^2$, $R^3$ and $R^4$, which may be the same or different, are each hydrogen or $C_{1-5}$ alkyl, X is ethylene or transvinylene, Y is $C_{1-5}$ alkyleneoxy, wherein the oxygen is bonded to $R^5$, or a direct bond, $R^5$ is phenyl or naphthyl which is unsubstituted or is substituted by one or more substituents selected from halogen, nitro, and $C_{1-5}$-alkyl, alkoxy and halogenalkyl, and n is 1 to 4, and for those compounds wherein $R^1$ is carboxy, the pharmaceutically or veterinarily acceptable salts thereof.

2. The prostane derivative of claim 1 wherein $R^2$, $R^3$ and $R^4$, which may be the same or different, are each hydrogen, methyl or ethyl, n is 1 or 2, Y is methyleneoxy, isopropyl-ideneoxy, methylethylene or a direct bond, $R^5$ is phenyl or naphthyl which is unsubstituted or substituted by one or two substituents selected from halogen and $C_{1-5}$ halogenoalkyl, and X is as defined in claim 1.

3. The prostane derivative of claim 2 wherein $R^2$ and $R^4$ are hydrogen, $R^3$ is hydrogen or methyl, X is transvinylene and $R^5$ is phenyl, chlorophenyl or trifluoromethylphenyl.

4. The prostane derivative of claim 3 wherein $R^1$ is carboxy or methoxycarbonyl, n is 1, and $R^5$ is phenyl, 3-chlorophenyl or 4-trifluoromethylphenyl.

5. The prostane derivative of claim 4 which is methyl 16-(3-chlorophenoxy)-9α,11α,15α-trihydroxy-17,18,19,20-tetranor-4-cis,13-trans-prostadienoate, methyl 16-(3-chlorophenoxy)-9α,11α,15β-trihydroxy-17,18,19,20-tetranor-4-cis,13-trans-prostadienoate, 16-(3-chlorophenoxy)-9α,11α,15-trihydroxy-17,18,19,20-tetranor-4-cis,13-trans-prostadienoic acid and methyl 16-(3-chlorophenoxy)-9α,11α,15-trihydroxy-16-methyl-18,19,20-trinor-4-cis, 13-trans-prostadienoate.

6. A pharmaceutical or veterinary composition comprising an effective amount of the prostane derivative of claim 1 together with a pharmaceutically or veterinarily acceptable diluent or carrier.

7. A method of inducing luteolysis, in a mammalian host requiring such treatment, which comprises administering to the host a luteolytically effective amount of the prostane derivative of claim 1.

8. The prostane derivative of claim 1 which is 16-(3-chlorophenoxy)-9α,11α,15-trihydroxy-17,18,19,20-tetranor-4-cis,13-trans-prostadienoic acid.

9. A prostane derivative of the formula

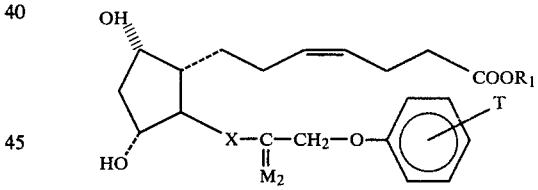

wherein $R_1$ is hydrogen or an alkyl of one of 12 carbon atoms, wherein M is H ⫶ OH or H ⫶ OH, wherein X is trans —CH═CH— or $CH_2$—$CH_2$—; wherein T is alkyl of 1-4 carbon atoms, fluoro, chloro, trifluoromethyl, or $OR_3$ wherein $R_3$ is an alkyl of one to 4 carbon atoms; and the pharmacologically acceptable salts thereof when $R_1$ is hydrogen.

* * * * *